(12) United States Patent
Erlandsson et al.

(10) Patent No.: US 11,065,160 B2
(45) Date of Patent: Jul. 20, 2021

(54) TREATED NONWOVEN HAVING AN AFFINITY FOR AN ACTIVE INGREDIENT

(71) Applicant: AVINTIV Specialty Materials Inc., Charlotte, NC (US)

(72) Inventors: Sven Krister Erlandsson, Advance, NC (US); Pierre Grondin, Mooresville, NC (US); Ralph A. Moody, III, Mooresville, NC (US)

(73) Assignee: AVINTIV Specialty Materials Inc., Charlotte, NC (US)

( * ) Notice: Subject to any disclaimer, the term of this patent is extended or adjusted under 35 U.S.C. 154(b) by 200 days.

(21) Appl. No.: 15/208,845

(22) Filed: Jul. 13, 2016

(65) Prior Publication Data

US 2017/0014282 A1 Jan. 19, 2017

Related U.S. Application Data

(60) Provisional application No. 62/191,847, filed on Jul. 13, 2015.

(51) Int. Cl.
*A61F 13/511* (2006.01)
*D04H 3/018* (2012.01)
(Continued)

(52) U.S. Cl.
CPC .. *A61F 13/51113* (2013.01); *A61F 13/15658* (2013.01); *A61F 13/511* (2013.01); *A61L 15/24* (2013.01); *A61L 15/44* (2013.01); *A61L 15/56* (2013.01); *D04H 3/016* (2013.01); *D04H 3/018* (2013.01); *A61F 2013/5109* (2013.01);
(Continued)

(58) Field of Classification Search
CPC .......... A61F 13/51113; A61F 13/15658; A61F 13/511; A61F 2013/51009; A61F 2013/51117; A61F 2013/51023; A61F 2013/51028; A61F 2013/5109; A61F 2013/15447; A61F 2013/51; A61F 2013/51038; A61F 2013/51052; A61F 13/42; A61F 2013/421; A61F 2013/427; A61F 2013/429; A61L 15/24;
(Continued)

(56) References Cited

U.S. PATENT DOCUMENTS 5,361,784 A 11/1994 Kinder
5,415,640 A * 5/1995 Kirby .................... A61F 13/512
604/366

(Continued)

FOREIGN PATENT DOCUMENTS

JP 2007518898 A 7/2007
JP 2007529291 A 10/2007
(Continued)

OTHER PUBLICATIONS

International Search Report and Written Opinion of corresponding International Application No. PCT/US2016/041994, dated Oct. 5, 2016, all enclosed pages cited.

(Continued)

*Primary Examiner* — Jennifer A Steele
(74) *Attorney, Agent, or Firm* — Burr & Forman LLP

(57) ABSTRACT

A nonwoven having a high affinity for an active ingredient is proved, the nonwoven having at least one high surface area fiber in addition to the active ingredient.

17 Claims, 4 Drawing Sheets

(51) Int. Cl.
*A61F 13/15* (2006.01)
*A61L 15/24* (2006.01)
*A61L 15/44* (2006.01)
*A61L 15/56* (2006.01)
*A61F 13/51* (2006.01)
*D04H 3/016* (2012.01)
*D04H 1/4391* (2012.01)

(52) U.S. Cl.
CPC ............ *A61F 2013/51009* (2013.01); *A61F 2013/51023* (2013.01); *A61F 2013/51028* (2013.01); *A61F 2013/51117* (2013.01); *A61L 2300/21* (2013.01)

(58) Field of Classification Search
CPC ...... A61L 15/56; A61L 15/44; A61L 2300/21; D04H 1/4374; D04H 3/018; D04H 1/4391; Y10T 442/20
USPC ........................................................ 604/361
See application file for complete search history.

(56) References Cited

U.S. PATENT DOCUMENTS

| | | | |
|---|---|---|---|
| 5,643,588 A | 7/1997 | Roe et al. | |
| 5,968,025 A | 10/1999 | Roe et al. | |
| 6,471,910 B1* | 10/2002 | Haggard | D01D 5/253 156/167 |
| 6,613,704 B1* | 9/2003 | Arnold | D04H 1/54 428/212 |
| 2003/0113289 A1 | 6/2003 | Hu et al. | |
| 2005/0215155 A1* | 9/2005 | Young | A61F 13/15203 442/337 |
| 2005/0227564 A1* | 10/2005 | Bond | B32B 5/08 442/337 |
| 2007/0287971 A1* | 12/2007 | Roe | A61F 13/42 604/361 |
| 2009/0130160 A1 | 5/2009 | Dugan | |
| 2010/0028638 A1* | 2/2010 | Reichardt | A61F 13/4902 428/219 |
| 2013/0071659 A1 | 3/2013 | Janke et al. | |
| 2013/0269294 A1* | 10/2013 | Benton | B32B 5/26 53/425 |
| 2014/0336605 A1 | 11/2014 | Hardie et al. | |

FOREIGN PATENT DOCUMENTS

| | | |
|---|---|---|
| JP | 2008542570 A | 11/2008 |
| JP | 2012522625 A | 9/2012 |
| JP | 2014091899 A | 5/2014 |
| WO | 2003016606 A1 | 2/2003 |
| WO | 2004044298 A1 | 5/2004 |
| WO | 2005095700 A1 | 10/2005 |
| WO | 2010017158 A1 | 2/2010 |

OTHER PUBLICATIONS

Second Written Opinion of corresponding International Application No. PCT/US2016/041994 dated Jun. 7, 2017, all enclosed pages cited.
Communication pursuant to Article 94(3) EPC from European application No. 16744616.0 dated Feb. 12, 2019, all enclosed pages cited.
English Translation of Office Action issued in corresponding Colombia Patent Application No. NC2018/0001251 dated Sep. 6, 2019, all enclosed pages cited.
Office Action issued in corresponding Chinese Patent Application No. 201680041293.5 dated May 7, 2020, all enclosed pages cited.
English Translation of Office Action issued in corresponding Chinese Patent Application No. 201680041293.5 dated May 7, 2020, all enclosed pages cited.
Office Action issued in corresponding Japanese Patent Application No. 2018-501240 dated Jul. 7, 2020, all enclosed pages cited.
English Translation of Office Action issued in corresponding Colombian Patent Application No. NC2018/0001251 dated Feb. 17, 2020, all enclosed pages cited.
First Examination Report issued in corresponding Australian Patent Application No. 2016291767 dated Jan. 28, 2020, all enclosed pages cited.

\* cited by examiner

TREATED NONWOVEN HAVING AN AFFINITY FOR AN ACTIVE INGREDIENT

PRIORITY CLAIM

This application claims priority under 35 U.S.C. § 119(e) to U.S. Provisional Application Ser. No. 62/191,847, filed on Jul. 13, 2015, which is expressly incorporated by reference herein in its entirety.

TECHNICAL FIELD

The presently-disclosed invention relates generally to nonwovens comprising an increased affinity to an active ingredient.

BACKGROUND

It is well known that active ingredients may be applied to nonwovens used in personal care products. A liner or topsheet incorporated into a diaper is an example of a nonwoven used in a personal care product. A liner or topsheet in a diaper is intended to contact the user and generally is configured to be permeable to the body fluids to be absorbed by the core of the diaper. An active ingredient may be included in the liner or topsheet to promote skin health. Examples of active ingredients include Aloe Vera, lanoline, petrolatum, moisturizers or even sealants. Examples of such approaches are described by U.S. Pat. Nos. 5,643,588 and 5,968,025.

The active ingredients included in the liner or topsheet may be chosen such that they may become leached to the core as the body fluids pass through the liner or topsheet to the core. Generally, active ingredients that are configured within the liner or topsheet to pass through to the core with the body fluids may also be for the additional purpose of maintaining a certain property of the bodily fluids. For example, active ingredients may be configured to control pH for the purpose of controlling bacterial growth or reducing odor from the bodily fluids.

The active ingredients may also be configured to be substantially fixed in the nonwoven preferably such that they are available at the surface of the fibers that contact the fluids passing through the nonwoven. Active ingredients substantially fixed, preferably concentrated towards the surface of the fibers of the nonwoven that contact the fluids may interact with the fluid (for example, air or a bodily fluid) that travels through the nonwoven. U.S. Pat. No. 6,652,845 teaches an example of an active ingredient that may be used for odor control, for example.

The active ingredient may be applied to the complete surface of the nonwoven or the active ingredient may be applied to only part of the nonwoven (e.g., along a strip pattern). The active ingredient conventionally has been applied to a carded web or a spunbond nonwoven that have typically been manufactured from fibers having diameters greater than about 14 microns and having a substantially round cross section. It is often desirable to coat those fibers of a nonwoven used as liner with a film of active ingredient while leaving the pores of that nonwoven opened to allow good liquid permeability. Such coating may also include a conventional surfactant to maintain the hydrophilicity of the product. It is often desirable to maximize the loading of active ingredient on the fibers because it can be beneficial in regard to the amount of that formulation that can be transferred to the skin by contact or can be eluted to the absorbent core when solubilized by a body fluid (e.g. urine).

In certain applications using a nonwoven having one or more active ingredients, it may be desired to increase the loading of active ingredient and/or the amount of active ingredient that becomes available to be transferred to one or more of the body having contact with the nonwoven or another layer of the product encompassing the nonwoven. For example, it may be desirable that the transfer of the active ingredient through contact with the skin leads to a more uniform distribution across the skin. Such an active ingredient has been conventionally coated on round shape filaments forming the nonwoven.

There remains a need in the art for a nonwoven that is suitable for personal care product or other products that allows an increased amount of an active ingredient to be captured and available per gram of fiber in the nonwoven while maintaining a suitable liquid permeability of the nonwoven. There also remains a need for such nonwoven that can, when used as in a personal care product or other products, that optimally transfers the active ingredient or ingredients to the skin to form a uniform coating.

SUMMARY OF INVENTION

One or more embodiments of the invention may address one or more of the aforementioned problems. Certain embodiments, according to the invention, provide a nonwoven comprising at least one high surface area fiber and at least one active ingredient. In one aspect, the nonwoven includes at least one nonwoven layer having a combination of a higher high surface area fiber and a lower high surface area fiber.

A nonwoven comprising at least one nonwoven layer; a high surface area portion (e.g., 100% or less than 100% of the nonwoven) comprising at least one high surface area fiber; and an active ingredient disposed substantially at the high surface area.

According to an embodiment of the invention, the at least one high surface area fiber comprises a fine denier round fiber having an average diameter less than about 14 microns or less than 12 microns according to another embodiment of the invention.

In certain embodiments of the invention, the nonwoven may additionally comprise a fine denier round fiber having an average diameter of greater than or equal to about 14 microns. The concentration of the fine denier round fiber having an average diameter of greater than or equal to about 14 microns may be less than about 50 wt % based upon a total weight of the nonwoven according to certain embodiments of the invention. The concentration of the fine denier round fiber having an average diameter of greater than or equal to about 14 microns may be less than about 20 wt % based upon a total weight of the nonwoven according to certain other embodiments of the invention.

In certain embodiments of the invention, the at least one high surface area fiber may comprise a fiber having a non-circular cross section. The fiber having a non-circular cross section may comprise any of a bilobal fiber, a trilobal fiber, a bowtie shaped fiber, a ribbon-shaped fiber, and any combination thereof.

Further pursuant to the embodiments when the at least one high surface area fiber comprises a ribbon shaped fiber, a width to thickness ratio greater than about 2.5 or greater than about 3.5 in yet other embodiments.

In certain embodiments of the invention, the at least one high surface area fiber may comprise a fine denier round fiber having an average diameter less than about 14 microns and a fiber having a non-circular cross section. In yet other embodiments of the invention, the at least one high surface area fiber may comprise a fine denier round fiber having an average diameter less than about 12 microns and a fiber having a non-circular cross section. In certain various embodiments of the invention, the non-circular cross section fiber may comprise any of a bilobal fiber, a trilobal fiber, a bowtie shaped fiber, a ribbon-shaped fiber, and any combination thereof. The ribbon shaped fiber may have a width to thickness ratio greater than about 2.5 according to certain embodiments of the invention, or a width to thickness ratio greater than about 3.5 in certain embodiments of the invention.

In certain embodiments of the invention, the at least one high surface area fiber comprising a fine denier round fiber having an average diameter less than about 14 microns and a fiber having a non-circular cross section. In yet other embodiments of the invention, the at least one high surface area fiber comprises a fine denier round fiber having an average diameter less than about 12 microns and a fiber having a non-circular cross section. Further pursuant to these embodiments of the invention, the fiber having a non-circular cross section may comprise one or more of a bilobal fiber, a trilobal fiber, a bowtie shaped fiber, and a ribbon-shaped fiber.

An active ingredient of the nonwoven of the invention may comprise any one or more of an ingredient having a beneficial impact on the skin; an ingredient that can modify the pH of a fluid; an ingredient that can control the growth an organism including antimicrobials, antifungals, etc. and any combination thereof; an ingredient that can absorb an odor causing compound from a fluid; an ingredient that can provide a signal upon coming in contact with a chemical species; and an ingredient that can provide a signal upon becoming exposed to a specific environmental condition including wetness, temperature, and combinations thereof. In a more specific embodiment of the invention, the active ingredient comprises at least one of a lactic acid and a salt thereof.

In another aspect, a nonwoven comprising two or more nonwoven layers is provided. According to an embodiment of the invention, the nonwoven comprises a first nonwoven layer comprising a low surface area fiber, a second nonwoven layer comprising at least one high surface area fiber, and an active ingredient disposed substantially at an available surface area of the nonwoven. In an embodiment of the invention, the second nonwoven layer is a meltblown layer.

In another aspect, a method of manufacturing a nonwoven is provided. According to an embodiment of the invention, the method for manufacturing a nonwoven comprises the steps of forming a nonwoven layer comprising at least one high surface area fiber, and disposing an active ingredient substantially at the high surface area.

According to another embodiment of the invention, the method for manufacturing a nonwoven comprises forming a first nonwoven layer comprising a low surface area fiber, forming a second nonwoven layer comprising at least one high surface area fiber, and disposing an active ingredient at an available surface area of the nonwoven. In certain embodiments of the invention, the second nonwoven layer is a meltblown later.

According to an embodiment of the invention, a topsheet for a hygiene product comprises at least one nonwoven layer; at least one high surface area fiber; and an active ingredient disposed substantially at the high surface area, wherein the active ingredient is selected such that upon coming in contact with a fluid it will migrate from the high surface area to a skin of a user of the hygiene product to control the pH at the skin. In certain embodiments of the invention, the active ingredient for controlling pH at the skin of the user of the hygiene product comprises at least one of a lactic acid and a lactic acid derivative. In another embodiment if the invention, the benefit to the skin is improved skin health and the active ingredient comprises any one or more of lanoline, aloe vera, lactic acid, and chamomile.

Another aspect provides a topsheet of a hygiene product comprising any one or more of the nonwovens of the invention.

Still other objects and features will become apparent from the following detailed description considered in conjunction with the accompanying drawings.

BRIEF DESCRIPTION OF THE DRAWING(S)

The invention now will be described more fully hereinafter with reference to the accompanying drawings; in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Figure 2A:
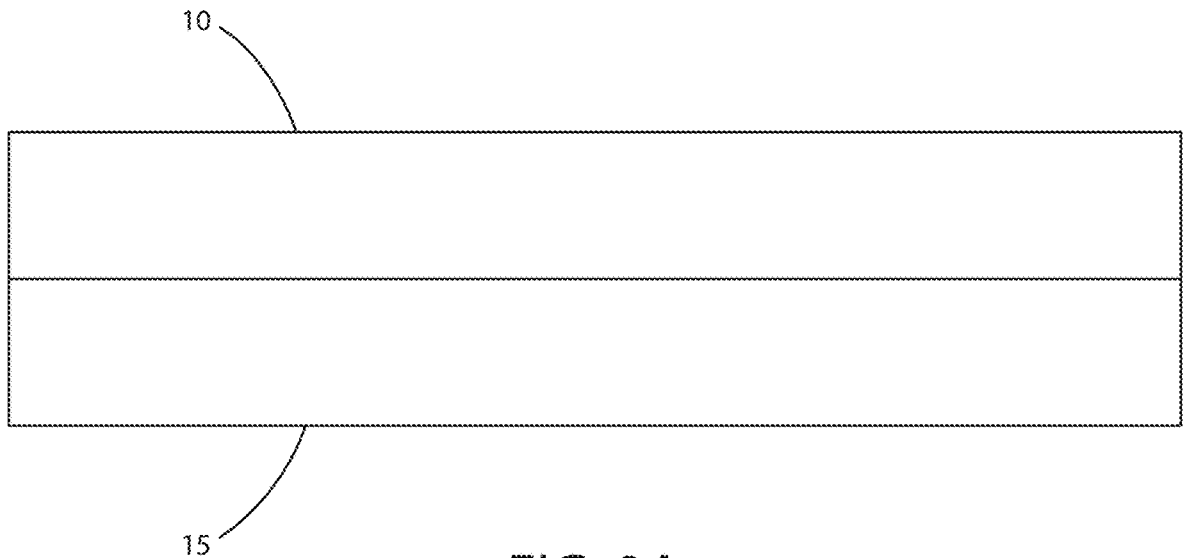
FIG. 2A is a cross-sectional view of a cut end of a fiber.
Figure 2B:
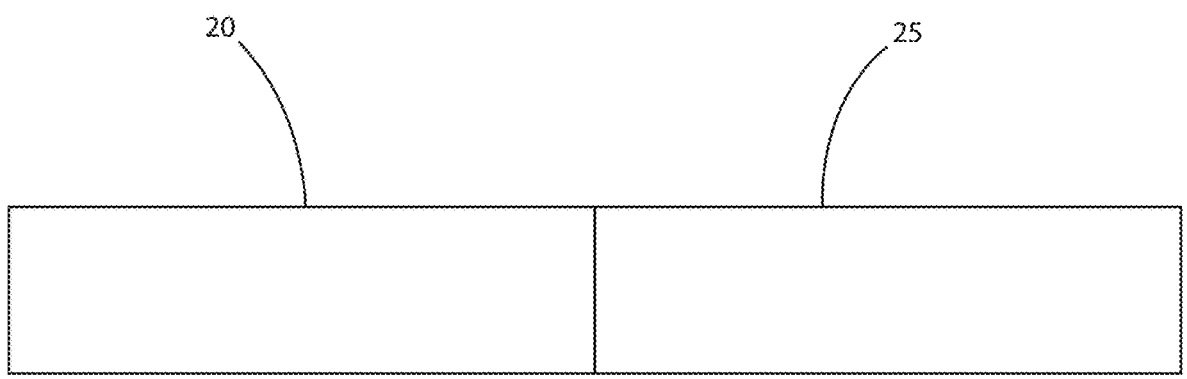
FIG. 2B is a cross-sectional view of a cut end of another fiber.
Figure 4:
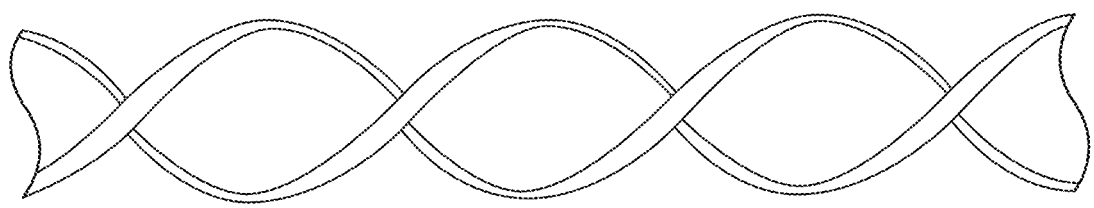

FIG. 4 is an isometric view of the fiber of FIG. 2B after undergoing heat treatment to trigger shrinkage to provide a ribbon fiber of a nonwoven according to another embodiment of the invention; and FIGS. 5A-F illustrate cross-sectional enlarged views of several different shapes of fibers, wherein FIGS. 5A-E showing various ribbon-shaped fibers in accordance with fibers used in the nonwovens of certain other embodiments of the invention.

DETAILED DESCRIPTION

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

It is to be understood, however, that the drawings are designed solely for purposes of illustration and not as a definition of the limits of the invention, for which reference should be made to the appended claims. Any relative dimensions illustrated in the figures are given by way of example and are not intended to be limiting. As would be appreciated by a person having ordinary skill in the art, the relative dimensions can vary depending on any number of factors including, without limitation, the intended use and performance of the illustrated article.

The invention includes, according to certain embodiments, a nonwoven-based product having at least one nonwoven layer, such that the at least one nonwoven layer has been configured to have an affinity for an active ingredient. In particular, the nonwovens of the invention may be useful as a liner or topsheet in certain hygiene products including, without limitation, for example, diapers.

The terms "substantial" or "substantially" may encompass the whole amount as specified, according to certain embodiments of the invention, or largely but not the whole amount specified according to other embodiments of the invention.

The terms "polymer" or "polymeric", as used interchangeably herein, may comprise homopolymers, copolymers, such as, for example, block, graft, random, and alternating copolymers, terpolymers, etc., and blends and modifications thereof. Furthermore, unless otherwise specifically limited, the term "polymer" or "polymeric" shall include all possible structural isomers; stereoisomers including, without limitation, geometric isomers, optical isomers or enantionmers; and/or any chiral molecular configuration of such polymer or polymeric material. These configurations include, but are not limited to, isotactic, syndiotactic, and atactic configurations of such polymer or polymeric material.

The terms "nonwoven" and "nonwoven web", as used herein, may comprise a web having a structure of individual fibers, filaments, and/or threads that are interlaid but not in an identifiable repeating manner as in a knitted or woven fabric. Nonwoven fabrics or webs, according to certain embodiments of the invention, may be formed by any process conventionally known in the art such as, for example, meltblowing processes, spunbonding processes, hydroentangling, air-laid, and bonded carded web processes.

The term "layer", as used herein, may comprise a generally recognizable combination of similar material types and/or functions existing in the X-Y plane.

The term "spunbond", as used herein, may comprise fibers which are formed by extruding molten thermoplastic material as filaments from a plurality of fine, usually circular, capillaries of a spinneret with the diameter of the extruded filaments then being rapidly reduced. According to an embodiment of the invention, spunbond fibers are generally not tacky when they are deposited onto a collecting surface and may be generally continuous. It is noted that the spunbond used in certain composites of the invention may include nonwoven described in the literature as SPIN-LACE®.

The term "meltblown", as used herein, may comprise fibers formed by extruding a molten thermoplastic material through a plurality of fine die capillaries as molten threads or filaments into converging high velocity, usually hot, gas (e.g. air) streams which attenuate the filaments of molten thermoplastic material to reduce their diameter, which may be to microfiber diameter, according to certain embodiments of the invention. According to an embodiment of the invention, the die capillaries may be circular. Thereafter, the meltblown fibers are carried by the high velocity gas stream and are deposited on a collecting surface to form a web of randomly disbursed meltblown fibers. Meltblown fibers are microfibers which may be continuous or discontinuous and are generally tacky when deposited onto a collecting surface.

The term "active ingredient", as used herein, is intended to include chemicals that interact with surfaces (e.g., skin) or fluids (e.g., urine) that come in contact with the fibers forming the nonwovens. While the nonwovens of the invention may include surfactants or other molecules that are used only to modify the wettability of the nonwoven, these surfactants or other molecules that are used only to modify the wettability of the nonwoven are generally not considered an active ingredient for the purposes of this disclosure. Non-limiting examples of active ingredients may include: an ingredient that is known to have a beneficial impact on the skin including lanoline, lactic acid, aloe vera, chamomile etc. and any combination thereof an ingredient that can modify the pH of a fluid or surface that comes in contact with the ingredient; an ingredient that can control the growth of or kill an organism including antimicrobials, antifungals, etc. and any combination thereof; an ingredient that can absorb an odor or odor causing compound from a fluid; and an ingredient that can provides a signal when coming in contact with a chemical species and/or becoming exposed to a specific environmental condition such as wetness, temperature, ammonia, etc. and combinations thereof.

According to an embodiment of the invention, the active ingredient comprises a pH controlling compound. In certain embodiments of the invention the additive is chosen from acetic acid, propionic acid, lactic acid, ascorbic acid, phenylalanine, citric acid, butyric acid, valeric acid, capronic acid, succinic acid and/or a salt thereof. According to an embodiment of the invention, for example, the salt is a sodium salt. Certain salts, in accordance with certain embodiments of the invention, include sodium propionate and sodium acetate.

As used herein, "fiber" means a staple fiber and/or a continuous filament. A fiber typically means an elongate particulate having an apparent length exceeding its apparent width, substantially exceeding according to certain embodiments of the invention. According to an embodiment of the invention, a length to diameter ratio of the fiber is at least about 10, at least about 20, at least about 25, at least about 40 at least about 50, and at least about 100.

A fiber that is "monocomponent" means a staple fiber and/or a continuous filament comprising at least about 85 weight percent of one polymer or copolymer or more than one polymer and/or copolymer in a blend, as further defined herein.

As used herein, "bicomponent fiber" means a fiber or a filament comprising a pair of distinct polymer components substantially aligned and adhered to each other along the length of the fiber. A cross-section of a bicomponent fiber may be, for example, a side-by-side, sheath-core or other suitable cross-section from which useful crimp can be developed. In preferred embodiments of the invention, the cross-section of the bicomponent fiber comprises a substantially side-by-side cross-section. A "multicomponent fiber" means a fiber or a filament comprising more than two polymer components.

The term "hydroentangle", as used herein, may comprise a process for bonding a nonwoven fabric by using high pressure water jets to intermingle the fibers. Several rows of water jets are directed against the fiber web, which is supported by a movable fabric. Fiber entanglements are introduced by the combined effects of the water jets and the turbulent water created in the web, which intertwines neighboring fibers.

The inventors have conceived that other shapes of fibers other than conventional round shaped fibers may be used in hygiene applications, for example, a liner or topsheet for a diaper, to promote the transfer of an active ingredient from such a nonwoven due to improved fiber-to-skin surface contact provided by the nonwoven. Applications outside of diapers using nonwovens that include such fibers have been contemplated by the inventors including, for example, nonwovens for feminine care products, incontinence products, and the like. Applications outside of hygiene use are also contemplated, including as a non-limiting example, wipes and gowns for medical care.

In an embodiment of the invention, a product for hygiene use comprises a topsheet or a liner comprising at least one nonwoven layer, a high surface area portion (e.g., 100% or less than 100% of the nonwoven) comprising at least one high surface area fiber, and an active ingredient disposed substantially at the high surface area, wherein the active ingredient is chosen such that the active ingredient will transfer and/or migrate from the high surface area to a fluid that comes in contact with the active ingredient to the skin of a wearer of the hygiene product. Specific to these embodiments, the active ingredient is chosen to at least one of have a beneficial impact on the skin of the user of the hygiene product, modify the pH of the surface of the skin of the user of the hygiene product, control the growth of or kill an organism at the surface of the skin of the user of the hygiene product, absorb an odor or odor causing compound at the skin of the user of the hygiene product; and provide a signal when coming in contact with a chemical species at the skin of the user of the hygiene product and/or becoming exposed to a specific environmental condition at the skin of the user of the hygiene product.

In a more specific embodiment of the invention, a product for hygiene use comprises a topsheet or a liner comprising at least one nonwoven layer, at least one high surface area fiber, and at least one of a lactic acid and a lactic acid derivative disposed substantially at the high surface area, wherein the at least one of the lactic acid and the lactic acid derivative transfers or migrates from the high surface area to a fluid that comes in contact with the at least one of the lactic acid and the lactic acid derivative to the skin of the user of the hygiene product to control the pH of the fluid at the surface of the skin of the user of the hygiene product.

The inventors have conceived that the transfer of one or more active ingredients through contact with the skin, resulting in more uniform contact with the skin by using fibers having shapes other that only round shaped fibers. The inventors have further conceived of a fiber blend including both fibers having a conventional round shape and other fibers that are substantially free of round shape fibers. In this regard, certain embodiments of the invention may comprise a fiber blend comprising round cross-sectional shaped fibers and non-round cross-sectional shaped fibers. In accordance with such embodiments of the invention, the transfer of one or more active ingredients through contact with skin may provide a more uniform application or coating of the one or more active ingredients onto the skin of a user.

The inventors have further conceived that fibers having shapes other than a round shape are capable of maximizing the loading of an active ingredient on the fibers. Without intending to be bound by theory, higher loadings of active ingredients on the fibers may be beneficial with respect to the amount of the active ingredient that may be available to be transferred to the skin by contact or that may elute to the absorbent core when solubilized by a body fluid (e.g. urine or other bodily fluid). For a given fiber of equal composition and decitex, for example, a substantially round cross section is the shape that produces the lowest ratio of fiber surface area per weight of polymer, while fibers substantially free of round shape cross section or even combinations of fibers having a round shape cross section and fibers substantially free of round shape cross section may maximize the capture of active ingredient and transfer of the active ingredient to either or both the core of the product comprising the nonwoven of the body (e.g., skin) that contacts the nonwoven.

According to an embodiment of the invention, the nonwoven of the invention having an affinity for an active ingredient may be used in a liner or a topsheet for a personal care product. Such personal care products may include, but are not limited to, a diaper; a feminine car product such as a sanitary napkin or a panty liner; an incontinence product; a nursing pad; a training pad; and other similar types of products. However, the nonwoven of the invention may have additional uses including, but not limited to, personal protective clothing, wipes, gowns and other nonwovens used in the medical field, as well as other similar types of products.

According to an embodiment of the invention, one or more active ingredients are disposed at the surface of the fibers or filaments of a nonwoven layer. Further pursuant to this embodiment of the invention, this configuration may provide a high surface area per gram of fiber and the one or more active ingredient(s) is/are permeable to body fluid. Without intending to be bound by theory, a high surface area allows the storage of more of the one or more active ingredients. In certain embodiments of the invention, the one or more active ingredients are disposed in a thin film that substantially surrounds the outer surface of the fibers or filaments of the nonwoven layer.

According to an embodiment of the invention, the fibers of the nonwoven have been selected according to the disclosure provided herein and the one or more active ingredients at the fiber surface have been configured to provide a high surface area of contact with the skin. Without intending to be bound by theory, a high surface area of contact may provide a rapid and more efficient transfer of the one or more active ingredients. For example, the rapid and more efficient transfer of the one or more active ingredients may result in a more consistent distribution of the one or more active ingredients that quickly develops at the skin of the wearer of the article that includes such a nonwoven, according to certain embodiments of the invention.

According to an embodiment of the invention, a liquid permeable nonwoven layer comprises fibers or filaments having at least one active ingredient disposed at least in part, according to certain embodiments of the invention, at or on the surface of the fibers or filaments (e.g., at least a portion of the surface of the fibers or filaments comprise at least one active ingredient disposed thereon). According to other embodiments of the invention, substantially all or all of the surface of the fibers or filaments comprises at least one active ingredient disposed thereon. In an embodiment of the invention, the fibers or filaments of the nonwoven are configured to provide a theoretical surface area (TS) that is greater than the TS for the fine denier spunbond conventionally found in nonwoven layers of similar products.

A finer denier round fiber or filament conventionally available typically averages about 1.4 dtex or more if made of polypropylene having an average diameter equal to or greater than 14 microns. Based on polypropylene, it may be calculated that such filaments have a theoretical surface area (TS) of about 3,142 $cm^2$ per gram of fiber. If the average diameter is reduced to about 12 microns for a polypropylene filament, the average decitex drops to about 1.03 and the TS is calculated as about 3,648 $cm^2$ per gram of fiber. A nonwoven having a reduced average diameter may be configured to capture and hold more active ingredient than a conventional nonwoven of round fibers having an average diameter of 14 microns or more. According to an embodiment, the nonwoven layer of the invention comprises fibers or filaments having an average diameter that is less than an average diameter of 14 microns further comprising an active ingredient that is disposed as a thin uniform film on the surface of the fibers and filaments to increase the availability of the active ingredient. According to an embodiment of the invention, the fibers and filaments or combination of a plurality of fibers and filaments have are configured to have a theoretical surface area (TS) greater than about 3,500 $cm^2$ per gram of fiber, greater than about 3,600 $cm^2$ per gram of fiber, greater than about 3,648 $cm^2$ per gram of fiber, greater than about 3,650 $cm^2$ per gram of fiber, greater than about 3,660 $cm^2$ per gram of fiber, greater than about 3,675 $cm^2$ per gram of fiber, greater than about 3,690 $cm^2$ per gram of fiber, greater than about 3,695 $cm^2$ per gram of fiber, greater than about 3,700 $cm^2$ per gram of fiber, greater than about 3,710 $cm^2$ per gram of fiber, greater than about 3,725 $cm^2$ per gram of fiber, greater than about 3,750 $cm^2$ per gram of fiber, greater than about 3,775 $cm^2$ per gram of fiber, greater than about 3,800 $cm^2$ per gram of fiber, greater than about 3,850 $cm^2$ per gram of fiber, greater than about 3,900 $cm^2$ per gram of fiber, greater than about 3,950 $cm^2$ per gram of fiber, greater than about 4,000 $cm^2$ per gram of fiber, greater than about 4,050 $cm^2$ per gram of fiber, greater than about 4,100 $cm^2$ per gram of fiber, greater than about 4,150 $cm^2$ per gram of fiber, greater than about 4,200 $cm^2$ per gram of fiber, greater than about 4,250 $cm^2$ per gram of fiber, greater than about 4,300 $cm^2$ per gram of fiber, greater than about 4,400 $cm^2$ per gram of fiber, and greater than about 4,500 $cm^2$ per gram of fiber, greater than about 4,750 $cm^2$ per gram of fiber or greater than about 5,000 $cm^2$ per gram of fiber. According to certain embodiments of the invention, in addition to providing these more favorable TS properties of the fibers or filaments, the fibers or filaments are additionally hydrophilic.

In accordance with an embodiment of the invention, a high surface area may be imparted to the nonwoven by including fibers having a finer decitex in the fabric. In accordance with certain other embodiments of the invention, a high surface area may be imparted to the nonwoven by including a fraction of the fibers, substantially all in certain embodiments, having a non-circular cross section—i.e., those exhibiting a greater surface area per unit of weight (e.g. theoretical $cm^2$ of fiber surface per gram of fiber). In accordance with yet certain other embodiments of the invention, a high surface area may be imparted to the nonwoven through varying combinations of including fibers have a finer decitex in the fabric and including a fraction, substantially all in certain embodiments, having a non-circular cross section—i.e., those exhibiting a greater surface area per unit of weight.

A non-limiting example of a nonwoven comprising finer fibers that increase the overall theoretical surface area would be a nonwoven comprising fibers having an average diameter that is small (e.g., less than about 12 microns in diameter according to certain embodiments, less than about 10 microns in diameter according to certain other embodiments, and from about 10 microns to about 12 microns in yet certain other embodiments). Another non-limiting example of a nonwoven comprising finer fiber that increase the overall theoretical surface area would be a nonwoven that comprises a combination of regular size fibers and finer fibers (e.g. meltblown fibers). For example, the nonwoven may have a SMS construction where the M is meltblown fibers with an average diameter substantially smaller than the S continuous filaments.

In certain embodiments of the invention, a nonwoven may comprise at least one fine denier fiber having an average diameter of less than about 14 microns and a fine denier fiber having an average diameter of greater than or equal to about 14 microns. The nonwoven may additionally comprise other types of fibers in combination with the fine denier fiber having an average diameter of less than about 14 microns and the fine denier fiber having an average diameter of greater than or equal to about 14 microns, according to certain embodiments of the invention. The fine denier fiber having an average diameter of greater than or equal to about 14 microns may have a concentration of less than about 5 wt %, less than about 10 wt %, less than about 15 wt %, less than about 20 wt %, less than about 25 wt %, less than about 30 wt %, less than about 40 wt %, less than about 50 wt %, less than about 60 wt %, less than about 75 wt %, less than about 90 wt %, less than about 95 wt %, or less than about 99 wt % based upon the overall weight of the nonwoven.

In certain embodiments of the invention, a nonwoven may comprise at least one fine denier fiber having an average diameter of less than about 12 microns and a fine denier fiber having an average diameter of greater than or equal to about 12 microns or a fine denier fiber having an average diameter of greater than or equal to about 14 microns according to another embodiment of the invention. The nonwoven may additionally comprise other types of fibers in combination with the fine denier fiber having an average diameter of less than about 12 microns and the fine denier fiber having an average diameter of greater than or equal to about 12 microns or the fine denier fiber having an average diameter of greater than or equal to about 14 microns, according to certain embodiments of the invention. Further pursuant to these certain embodiments of the invention, the fine denier fiber having an average diameter of greater than or equal to about 12 microns or the fine denier fiber having an average diameter of greater than or equal to 14 microns in certain other embodiments may have a concentration of less than about 5 wt %, less than about 10 wt %, less than about 15 wt %, less than about 20 wt %, less than about 25 wt %, less than about 30 wt %, less than about 40 wt %, less than about 50 wt %, less than about 60 wt %, less than about 75 wt %, less than about 90 wt %, less than about 95 wt %, or less than about 99 wt % based upon the overall weight of the nonwoven.

In accordance with certain embodiments of the invention, the at least one nonwoven layer may comprise a spunbond layer. In certain embodiments, for example, the at least one nonwoven layer may be devoid of a meltblown layer. In some embodiments, for instance, the at least one nonwoven layer may comprise synthetic polymer filaments. In such embodiments, for example, the synthetic polymer filaments may comprise at least one of a polyolefin, a polyester, a polyamide, or any combination thereof. According to certain embodiments, for instance, the synthetic polymer filaments may comprise at least one of polyethylene, polypropylene, partially aromatic or fully aromatic polyesters, polyhexamethylene diadipamide, polycaprolactam, aromatic or partially aromatic polyamides, aliphatic polyamides, or any combination thereof. In some embodiments, for example, the synthetic polymer filaments may comprise polypropylene.

According to certain embodiments of the invention, for instance, the synthetic polymer filaments may have an average diameter of less than about 14 microns, less than about 12 microns, or less that about 10 microns. In further embodiments, for example, the synthetic polymer filaments may have diameters comprising a range of from about 10 to about 14 microns, from about 12 to about 14 microns, or from about 10 to about 12 microns.

A non-limiting example of a nonwoven comprising a fraction of fibers having non-circular cross sections would be nonwovens comprising bilobal fibers and filaments and/or multilobal (trilobal, quadrulobal, etc.) fibers and filaments. Certain embodiments of the invention may comprise fibers having various cross sections, including round and ribbon as well as other cross sections. These fibers may have various sizes and/or diameters in accordance with the disclosure provided herein.

Figure 1A:
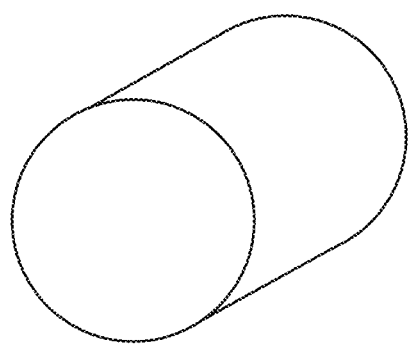
FIGS. 1A-1F are schematic views depicting various cross sections of various fibers of various nonwovens according to various embodiments of the invention.
Figure 1B:
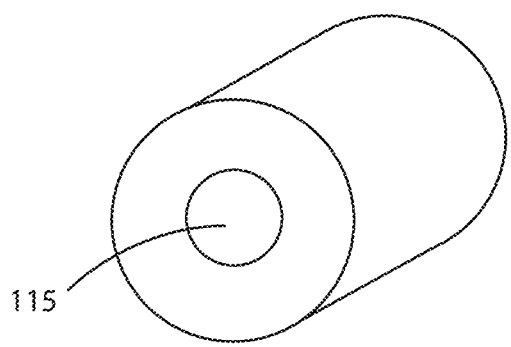
Figure 1C:
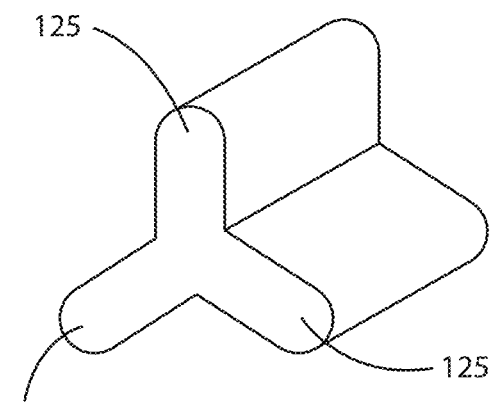
Figure 1D:
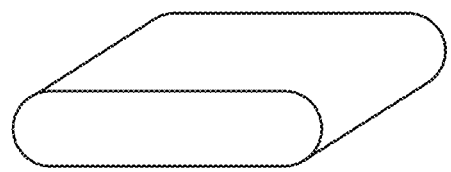
Figure 1E:
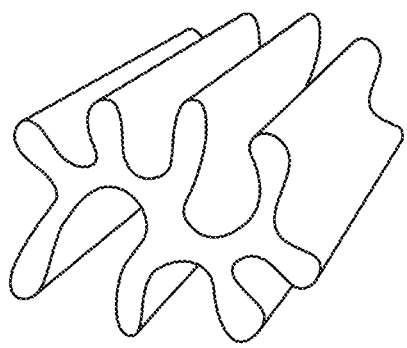
Figure 1F:
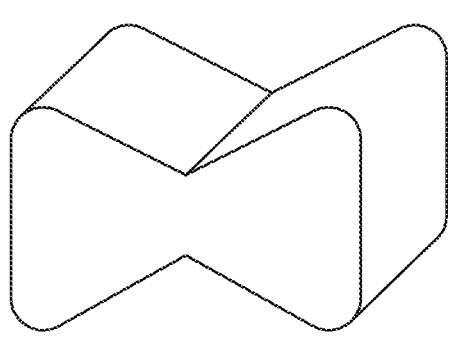

Various embodiments of cross-sections of fibers that may be used in the invention are represented in FIGS. 1A-1F. FIG. 1A illustrates a solid round or circular cross-section. FIG. 1B illustrates a round cross section having a void 115 that runs substantially along the entire length of the fiber. FIG. 1C illustrates a trilobal fiber having three arms 125 projecting from a center. FIG. 1C is representative of a trilobal fiber having arms 125 that are substantially the same. Other variations not illustrated include a trilobal fiber having arms of varying dimensions and positions. FIG. 1D illustrates a bilobal fiber. FIG. 1E illustrates a multilobal fiber having a plurality of arms extending from the fiber. FIG. 1F illustrates a fiber having a bowtie cross section.

Figure 3:
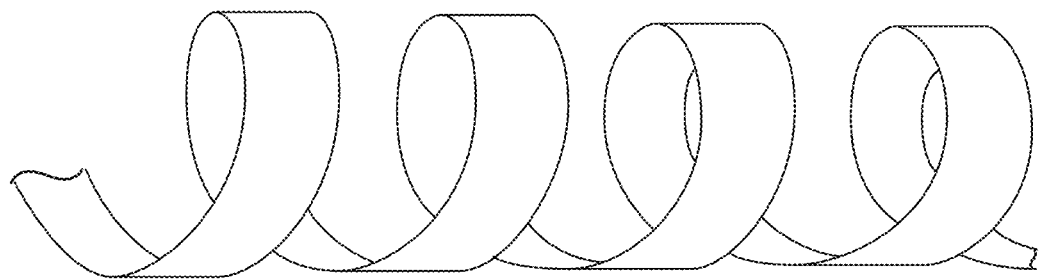
FIG. 3 is an isometric view the fiber of FIG. 2A after undergoing heat treatment to trigger shrinkage to provide a ribbon fiber of a nonwoven according to an embodiment of the invention.

According to an embodiment of the invention, one or more of the fibers or filaments of the nonwoven layer may comprise two polymer components, a first polymer component 10 and a second polymer component 15, having differing properties, such as differential shrinkage coefficients, for example, are positioned in a side-by-side configuration as illustrated in FIG. 2A. The fiber or filaments as illustrated in FIG. 2A shrinks in such a way similar to the crimped fiber represented in FIG. 3. According to this embodiment of the invention, such a fiber will shrink in a more predictive way, producing a more compact structure that is more difficult to compress that the regular round self-crimped bicomponent fiber.

According to another embodiment of the invention, the two polymer components may comprise a first polymer component 20 and a second polymer component 25 having different properties, such as differential shrinkage coefficients, for example, are positioned in a side-by-side configuration as illustrated in FIG. 2B. When heated and shrank the fiber of FIG. 2B will take a helix shape that rotate around the axis corresponding to the interface between the two polymer components similar, for, example, to the crimped fiber represented in FIG. 4. In accordance with certain embodiments of the invention, this approach produces a compact structure with good resistance to compression.

Figure 5A:
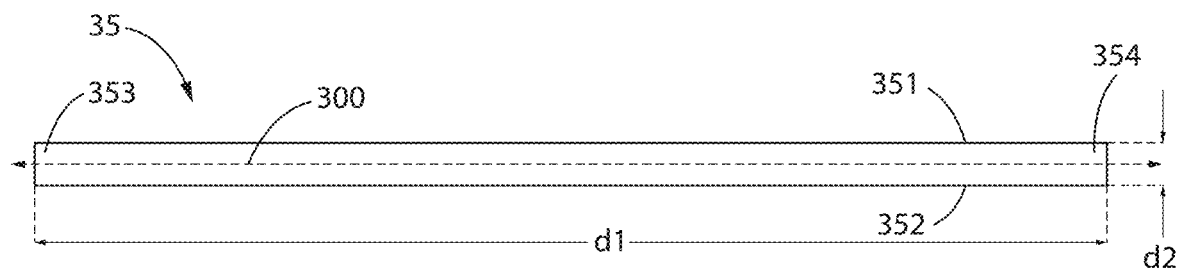

As used herein, the term "ribbon-shaped" refers to a cross-sectional geometry and aspect ratio. With respect to the cross-sectional geometry, "ribbon-shaped" refers to a cross-section that includes at least one pair (set) of symmetrical surfaces. For example, the cross section can be a polygon which includes two different pairs of opposite symmetrical surfaces or only one set thereof. By way of example, but without intending to be limiting, with reference FIG. 5A shows, the overall shape 35 has an imaginary major bisector 300, and a minor bisector (not shown), which is perpendicular to the major bisector, wherein opposite surfaces 351 and 352 are symmetrical surfaces with respect to each other with reference to the imaginary bisector 300. Other ribbon-shape geometries having at least one set of symmetrical surfaces are illustrated, for example, as shown in in FIGS. 5B-5E. The major bisector 300 can be straight (e.g., FIGS. 5A-5D), curvilinear (e.g., FIG. 5E), or other shapes, depending on the cross-sectional shape of the fiber.

In certain embodiments of the invention, the major bisector 300 may define shape of the "ribbon-shaped" fiber.

Figure 5B:
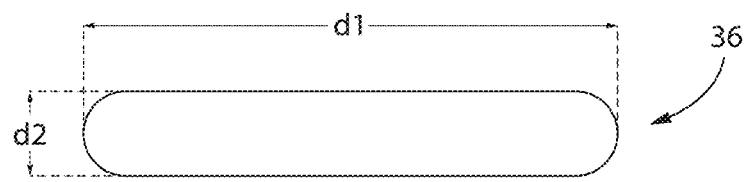
Figure 5C:
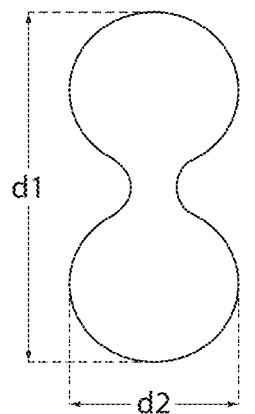
Figure 5D:
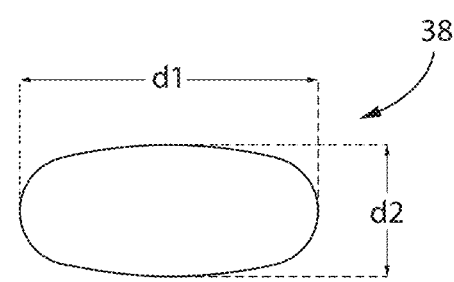
Figure 5E:
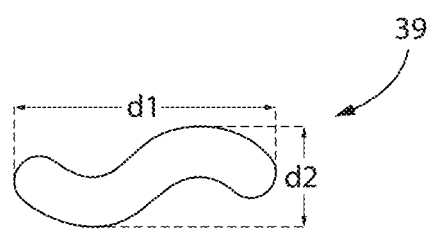
Figure 5F:
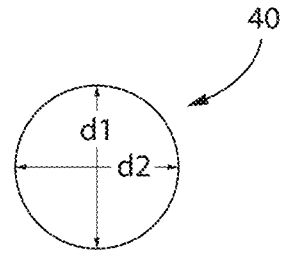

"Ribbon-shaped" may include, for example, a shape having two sets of parallel surfaces forming a rectangular shape (e.g. FIG. 5A). "Ribbon-shaped" may also include, for example, a cross-section having one set of parallel surfaces, which can be joined to one another by shorter rounded end joints having a radius of curvature (e.g., FIG. 5B). "Ribbon-shaped" additionally may include, for example, "dog-bone" shaped cross-sections, such as illustrated in FIG. 5C, and oval or elliptical shaped cross-sections, such as illustrated in FIG. 5D. In these cross-section illustrated in FIG. 5C, for example, the term "ribbon-shaped" refers to a cross-section that includes sets of symmetrical surfaces that comprise rounded (e.g. curvilinear or lobed) surfaces, that are diametrically oppositely to one another. As illustrated in FIG. 5D, the oval shaped cross-sections can have rounded or curvilinear type top and bottom symmetrical surfaces, which are joined to one another by shorter rounded end joints at the sides having a relatively smaller radius of curvature than the top and bottom symmetrical surfaces.

The term "ribbon-shaped" also includes cross-sectional geometry that includes no more than two square ends, or round ends, or "lobes" along the perimeter of the cross-section. FIG. 5C, for example, shows a bilobal cross section. The lobes differ from the indicated rounded end joints included in the cross-sections such as shown in FIGS. 5B and 5D referred to above. Surface irregularities like bumps or striations or embossed patterns that are relatively small when compared to the perimeter of the cross-section, or are not continuous along the length of the fibers are not included in the definition of "lobes," or the rounded end joints. It can also be understood that the above definition of "ribbon-shaped" covers cross-sectional geometries where one or more of the sets of surfaces (e.g., the opposite lengthwise surfaces) are not straight (e.g. FIG. 5E), provided such cross-sectional geometries meet the aspect ratio requirements as defined below.

With respect to aspect ratio, in certain embodiments of the invention, a "ribbon-shaped" cross-section has an aspect ratio (AR) of greater than 1.5:1. The aspect ratio is defined as the ratio of dimension d1 and dimension d2. Dimension d1 is the maximum dimension of a cross-section, whether ribbon-shaped or otherwise, measured along a first axis. Dimension d1 is also referred to as the major dimension of the ribbon-shaped cross-section. Dimension d2 is the maximum dimension of the same cross-section measured along a second axis that is perpendicular to the first axis that is used to measure dimension d1, where dimension d1 is greater than dimension d2. Dimension d2 is also referred to as the minor dimension. As an option, the major bisector 300 can lie along the first axis and the minor bisector (not shown) can lie along the second axis. Examples of how dimensions d1 and d2 are measured are illustrated in FIGS. 5A, 5B, 5C, 5D, and 5E, which illustrate ribbon-shaped cross-sections and in FIG. 5F which illustrates a non-ribbon-shaped cross-section as described below. Aspect ratio is calculated from the normalized ratio of dimensions d1 and d2, according to formula (I):

$$AR=(d1/d2):1 \qquad (I)$$

where the units used to measure d1 and d2 are the same.

A nonwoven of the invention may comprise a ribbon filament, optionally in combination with one or more fibers having a shape that is not of a ribbon form, the ribbon filament defined in terms of its a width to thickness ratio. According to an embodiment of the invention the width to thickness ratio of the ribbon filament is greater than about 2.5, preferably greater than about 3.0, or more preferably greater than about 3.5.

In certain embodiments of the invention, the polymer components of the ribbon fiber respectively comprise two polyolefins that are different—in a non-limiting example, a polyethylene and a polypropylene. In an embodiment of the invention, the polyolefins may comprise polyethylene terephthalate/polyethylene (PET/PE), polylactic acid/polyethylene (PLA/PE), or polyethylene terephthalate/polylactic acid (PET/PLA).

In certain embodiments of the invention, the polymer components may comprise copolymers, either in part or as a main polymer component. By way of example, without intending to be limiting, an ethylene polymer may comprise polymers composed mainly of ethylene such as high pressure process polyethylene or medium or low pressure process polyethylene, and may include not only ethylene homopolymers, but copolymers of ethylene, either in part or even as a main component, with propylene, butene-1, vinyl acetate or the like, and any combination thereof.

In an embodiment of the invention, the polymers of the first polymer component and second polymer component may respectively comprise any one or more of an isotactic polymer, a syndiotactic polymer, an isotactic-atactic stereo block polymer, and/or an atactic polymer. For example, without intending to be limiting, the polymers may comprise isotactic polypropylene and syndiotactic polypropylene, respectively, or polyethylene having different densities or tacticities, when applicable.

Pursuant to certain embodiments of the invention where the polymers of either or both polymer compositions comprise polyethylene, the polyethylene may be a linear, semi-crystalline homopolymer of ethane, e.g., high density polyethylene (HDPE); a random copolymer of ethylene and alpha-olefins, e.g., a linear low-density polyethylene (LLDPE); a branched ethylene homopolymer, e.g., a low density polyethylene (LDPE) or very low density polyethylene (VLDPE); an elastomeric polyolefin, e.g., a copolymer of propylene and alpha olefin; and any combination thereof.

In an embodiment of the invention, the polymers of the polymer components may be the same type of polymer but have different number average molecular weights. For example, the number average molecular weight of a first polymer of the first polymer component may be at least about 10,000, at least about 50,000, at least about 100,000, or at least about 500,000, alternatively, up to about 500,000, up to about 100,000, up to about 50,000, or up to about 10,000. The number average molecular weight of a second polymer of the second polymer component may be at least about 5,000, at least about 10,000, at least about 50,000, at least about 100,000, or at least about 500,000, alternatively, up to about 500,000, up to about 100,000, up to about 50,000, up to about 10,000 or up to about 5,000. However, the number average molecular weight of the first polymer differs from the number average molecular weight of the second polymer. The number average molecular weight of the first polymer may differ from the number average molecular weight of a second polymer by up to about 500, up to about 1,000, up to about 2,000, up to about 2,500, up to about 3,500, up to about 5,000, up to about 7,500, up to about 10,000, up to about 15,000, up to about 25,000, up to about 30,000, up to about 35,000, up to about 40,000, up to about 45,000, up to about 50,000, up to about 60,000, up to about 70,000, up to about 75,000, up to about 90,000, up to about 100,000, up to about 125,000, up to about 150,000, up to about 175,000, up to about 200,000, or up to about 250,000.

In an embodiment of the invention, in addition to the first polymer of the first polymer component and the second polymer of a second polymer component, either or both of the first polymer component and the second polymer component may include another polymer to form a polymer blend.

In certain embodiments of the invention, a nonwoven may comprise at least one non-circular cross section fiber and a circular cross section fiber. The nonwoven may additionally comprise other types of fibers in combination with the at least one non-circular cross section fiber and the circular cross section fiber. According to certain embodiments of the invention, the circular cross section fiber may have a concentration of less than about 5 wt %, less than about 10 wt %, less than about 15 wt %, less than about 20 wt %, less than about 25 wt %, less than about 30 wt %, less than about 40 wt %, less than about 50 wt %, less than about 60 wt %, less than about 75 wt %, less than about 90 wt %, less than about 95 wt %, or less than about 99 wt % based upon the overall weight of the nonwoven.

"Repeat Strike-Through" may be used to define the appropriate permeable nonwoven as suitable as liner for a personal care product and, more precisely for a hygienic product. In order to be suitable for some hygienic applications such as diapers, for example, a product would preferably have a strike through time that is less than 10 seconds for all of the three insults when tested as per WSP 70.7 (05) test method (definition as further provided herein). This constraint can be achieved by using a porous media that is hydrophilic and reasonably permeable or, by having apertures in the liner that would allow the fluid to go through regardless of whether the fibers have been treated with a surfactant or not. To get the hydrophilic property, a formulation comprising surfactant can be topically applied to the nonwoven or melt dispersed into the polymer prior to or while it is being formed into fibers.

In another embodiment of the invention, the fibers for the liner or topsheet are selected to provide an increased amount of surface contact with the skin of the user of the product. In a non-limiting exemplary embodiment of the invention, the nonwoven comprises a ribbon fiber having a width to height ratio of greater than 2.5, preferably at or greater than about 3.0, or more preferably at or greater than about 3.5. While not intending to be limited by the theory, the coating on the ribbon fibers will be more readily transferred to the user and available in a greater quantity than for round fibers or other fibers that do not provide the extent of surface area per weight of the nonwoven due to the enhanced contact with the wearer.

A non-limiting example embodiment of a nonwoven made from ribbon filaments is marketed under the name NUVIBOND® and offered by AVINTIV Specialty Materials, Inc. of Charlotte, N.C. A NUVIBOND nonwoven may comprise a ribbon fiber having a width to thickness ratio greater than 2.5. Sample 2 of the examples is a NUVIBOND nonwoven comprising a ribbon fiber having a width to thickness ratio greater than 2.5—specifically, about 3.5.

In another aspect, the invention provides a method of manufacturing a nonwoven having an affinity for an active ingredient. In accordance with certain embodiments of the invention, for instance, the method may further comprise meltspinning a polymer composition and forming the at least one nonwoven layer.

According to another embodiment of the invention, the method for manufacturing a nonwoven comprises forming a first nonwoven layer comprising a low surface area fiber, forming a second nonwoven layer comprising at least one high surface area fiber, and disposing an active ingredient at an available surface area of the nonwoven. In certain embodiments of the invention, the second nonwoven layer is a meltblown layer.

In accordance with certain embodiments of the invention, for instance, the at least one nonwoven layer may comprise a spunbond layer. In certain embodiments, for example, the at least one nonwoven layer may be devoid of a meltblown layer. In certain other embodiments, for example, the nonwoven may comprise a meltblown layer. In some embodiments, for instance, the at least one nonwoven layer may comprise synthetic polymer filaments. In such embodiments, for example, the synthetic polymer filaments may comprise at least one of a polyolefin, a polyester, a polyamide, or any combination thereof. According to certain embodiments, for instance, the synthetic polymer filaments may comprise at least one of polyethylene, polypropylene, partially aromatic or fully aromatic polyesters, polyhexamethylene diadipamide, polycaprolactam, aromatic or partially aromatic polyamides, aliphatic polyamides, or any combination thereof. In some embodiments, for example, the synthetic polymer filaments may comprise polypropylene.

According to certain embodiments of the invention, for instance, the synthetic polymer filaments may have an average diameter of less than about 14 microns, preferably, less than about 12 microns, and more preferably, less than about 10 microns. In further embodiments, for example, the synthetic polymer filaments may have a diameter ranging from about 10 to about 14 microns, from about 12 to about 14 microns, or from about 10 to about 12 microns.

According to certain embodiments of the invention, for example, the nonwoven fabric may have a basis weight comprising from about 10 to about 60 gsm. In further embodiments, for instance, the nonwoven fabric may have a basis weight comprising from about 10 to about 40 gsm. In other embodiments, for example, the nonwoven fabric may have a basis weight comprising from about 10 to about 30 gsm. In certain embodiments, for instance, the nonwoven fabric may have a basis weight comprising about 15 gsm. As such, in certain embodiments, the nonwoven fabric may have a basis weight comprising from at least about any of the following: 8, 10, 12, and 15 gsm.

According to certain embodiments of the invention, for example, the nonwoven fabric may comprise at least one nonwoven layer having a basis weight from about 1 to about 20 gsm. In further embodiments, for instance, the nonwoven fabric may comprise at least one nonwoven layer having a basis weight from about 5 to about 15 gsm. In other embodiments, for example, the nonwoven fabric may comprise at least one nonwoven layer having a basis weight from about 7 to about 12 gsm. In certain embodiments, for instance, the nonwoven fabric may comprise at least one nonwoven layer having a basis weight of about 10 gsm. As such, in certain embodiments, the nonwoven fabric may comprise at least one nonwoven layer having a basis weight from at least about any of the following: 1, 5, 7, and 10 gsm and/or at most about 20, 15, 12, and 10 gsm (e.g., about 5-15 gsm, about 10-12 gsm, etc.).

Strike through is defined as per EDANA/INDA Worldwide Strategic Partners standard tests WSP 70.7 (05) "Standard Test Method for Nonwovens—Repeat Liquid Strike-Through time" ("WSP 70.7"). The WSP 70.7 tests can be performed using a Lister AC by Lenzing Instruments GmbH & Co KG, Lenzing, Austria. For the WSP 70.7 test method, the strike through time for insult of 5 ml of a 0.9% saline solution is recorded in seconds after the first, second and third insult. Paper used for the absorbent core was type ERT FF3 supplied by Hollingworth & Vose, Winchcombe, England.

A non-limiting, example of a nonwoven in accordance with certain embodiments of the invention is configured according to the disclosure provided herein to provide a high theoretical surface area (TS) above 3500 $cm^2/g$, comprising at least one active ingredient and having sufficient porosity to a saline solution to be characterized as having a strike through time that is about 20 seconds or less, preferably about 15 seconds or less, or more preferably about 10 seconds or less at any of the three insults.

Another non-limiting, example of a nonwoven in accordance with certain embodiments of the invention comprises on the side exposed to the user at least one type of ribbon filament, optionally in combination with one or more fibers having a shapes that is not of a ribbon form, the at least one type of ribbon filament having a width to thickness ratio greater than about 2.5, preferably greater than about 3.0, or more preferably greater than about 3.5 and also comprising at least one active ingredient that is intended to be transferred to a surface of the filaments, the nonwoven exhibiting a strike through time that is about 20 seconds or less, preferably about 15 seconds or less, or more preferably about 10 seconds or less at any of the three insults.

As a person of ordinary skill in the art would understand having the benefit of this disclosure, the theoretical surface of the fibers of a nonwoven may be calculated based upon the density of polymer and the cross section shape and dimensions of the one or more types of fibers of the nonwoven.

Examples

Tables 1A and 1B summarize the information for one comparative and a few inventive theoretical examples, the latter being based on fine fibers or a blend of fine and large fibers.

TABLE 1A

|  |  | Fiber cross-section shape | Composition of nonwoven % |
| --- | --- | --- | --- |
| Comparative Sample | Nonwoven layer | round | 100 |
| Sample 1 | Nonwoven layer | round | 100 |
| Sample 2 | Nonwoven layer | ribbon | 100 |
| Sample 3 | Spunbond filament | round | 95 |
|  | Meltblown filament | round | 5 |

TABLE 1B

| | Fiber size decitex | Fiber diameter microns | Fiber width microns | Fiber thickness microns | Fiber circumference cm | Fiber length cm/g |
|---|---|---|---|---|---|---|
| Comparative Sample | 1.4 | 14 | | | 0.00440 | 714,286 |
| Sample 1 | 0.95 | 11.535 | | | 0.00362 | 1,052,632 |
| Sample 2 | 1.4 | NA | 23.21 | 6.63 | 0.005969 | 714,286 |
| Sample 3 | 1.502 | 14.5 | | | 0.004555 | 665,779 |
| | 0.0145 | 1.5 | | | 0.000471 | 65,108,500 |

TABLE 2

| | Theoretical Surface Area cm²/g | Combined cm²/g |
|---|---|---|
| Comparative Sample | 3,142 | — |
| Sample 1 | 3,815 | — |
| Sample 2 | 4,263 | — |
| Sample 3 | 3,032 | 4,510 |
| | 32,567 | |

Table 2 provides the theoretical surface area for 1 gram of the fibers of the samples referenced in Tables 1A and 1B.

The Comparative Sample of the tables is a nonwoven comprising 1.4 decitex round filaments, where the filaments comprises 1.4 gram of polymer per 10,000 meter of length or 1,000,000 of cm of length corresponding to a length of 714,285 cm per g. If the polymer is polypropylene having a density of 0.91 g/cm³, these filaments would have an average diameter of about 14 microns or 0.0014 cm. The average circumferential perimeter of such fibers is about 0.00440 cm. The Theoretical Surface or TS is calculated based upon the product of the perimeter and average of length of fibers per gram of fibers. Thus, the TS of the Comparative Sample, which is representative of the TS of nonwovens conventionally known in the art, is about 3,141 cm²/g. Of course, as a person having ordinary skill in the art would appreciate, this is a theoretical surface as bonding will compress fibers surrounding the bonding points and, where the fibers touch, the entire theoretical surface may not be available to be coated with an additive.

Sample 1, representing one example embodiment of the invention, is a nonwoven comprising 0.95 decitex round filaments whose filaments comprise about 0.95 gram of polymer per 10,000 meter of length or 1,000,000 cm of length of fibers corresponding to a length of 1,052,632 cm per gram. If the polymer is polypropylene having a density of about 0.91 g/cm³, the filaments will have an average diameter of about 11.535 micron or 0.0011535 cm. The circumferential perimeter of these filaments is about 0.003624 cm. Again, the TS may be calculated by taking the product of the perimeter and length per g and resulting in a TS of about 3,815 cm²/g.

Sample 2, representing another example embodiment of the invention, is a nonwoven fabric comprising a 1.4 dtex ribbon shape filament having a width to height ratio of about 3.5. The filaments are made of polypropylene having a density of about 0.91 g/cm³. For this calculation the rounding of the filament edges is ignored as it is considered to have only a small impact of the TS. The average thickness of the ribbon shape filaments of Sample 2 is about 0.000663 cm or 6.63 microns while the average width of the ribbon shape filaments is about 0.002321 cm or 23.2 microns. The TS cross section of this filament is calculated to be about 4,263 cm²/g.

Sample 3, representing yet another example embodiment of the invention, is a nonwoven fabric comprising 95% by weight of round filaments made of polypropylene having a density of about 0.91 g/cm³ and an average diameter of about 14.5 microns and, also comprises 5% by weight of meltblown filaments made of polypropylene having a density of about 0.91 g/cm³ and an average diameter of 1.5 micron. The combined TS area based upon the contributions from the spunbond and the meltblown layers is calculated to be about 4,510 cm²/g.

As the samples show, the TS of the nonwoven may be increased by using round shape conventional fibers but having smaller average diameters than have conventionally been used in the art, a combination of round shape and other shaped fibers (for example ribbon shape as illustrated in the examples) having greater available surface area, and a multilayer product where at least one layers includes finer fibers (for example, a meltblown layer). Of course, many additional combinations may be contemplated based upon the disclosure provided herein.

These and other modifications and variations to the invention may be practiced by those of ordinary skill in the art without departing from the spirit and scope of the invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

That which is claimed:

1. A nonwoven comprising:
    (a) at least a first spunbond nonwoven layer comprising a fiber blend of round cross-sectional shaped spunbond fibers and non-round cross-sectional shaped spunbond fibers, wherein the round cross-sectional shaped fibers have an average diameter less than 10 microns; and
    (b) an active ingredient disposed substantially at a surface of the fiber blend;
    wherein the nonwoven is devoid of a meltblown layer; and
    wherein the first nonwoven has a strike through time that is less than 10 seconds for all three insults when tested per WSP 70.7(05); and wherein the first nonwoven layer has a theoretical surface area of greater than about 4200 cm² per gram of fiber blend.

2. The nonwoven according to claim 1, wherein the non-round cross-sectional shaped fibers comprise a ribbon-shaped fiber.

3. The nonwoven according to claim 2, wherein the ribbon shaped fiber comprises a width to thickness ratio greater than about 2.5.

4. The nonwoven according to claim 1, wherein the active ingredient comprises an ingredient having a beneficial impact on skin, an ingredient that can modify the pH of a fluid, an ingredient that can control the growth an organism, or an ingredient that can absorb an odor causing compound from a fluid.

5. The nonwoven according to claim 1, wherein the active ingredient comprises an ingredient that can provide a signal upon coming in contact with a chemical species.

6. The nonwoven according to claim 1, wherein the active ingredient comprises an ingredient that can provide a signal upon becoming exposed to a specific environmental condition comprising wetness, temperature, or both.

7. The nonwoven according to claim 1, wherein the active ingredient comprises at least one of a lactic acid or a salt thereof.

8. The nonwoven according to claim 1, wherein the nonwoven comprises a topsheet disposed within a hygiene product.

9. The nonwoven according to claim 1, wherein the first nonwoven layer has a theoretical surface area of greater than about 4250 cm² per gram of fiber blend and less than about 5000 cm² per gram of fiber blend.

10. The nonwoven according to claim 1, wherein the first nonwoven layer has a theoretical surface area of greater than about 4500 cm² per gram of fiber blend.

11. The nonwoven according to claim 1, wherein the fiber blend has from 75 wt. % to 99 wt. % of round cross-sectional shaped spunbond fibers.

12. The nonwoven according to claim 1, wherein the first spunbond nonwoven comprises apertures such that fluid can pass through the apertures.

13. The nonwoven according to claim 1, wherein the first spunbond nonwoven comprises a hydrophilic additive.

14. The nonwoven according to claim 13, wherein the hydrophilic additive is melt dispersed within the fiber blend of round cross-sectional shaped spunbond fibers and non-round cross-sectional shaped spunbond fibers.

15. The nonwoven according to claim 13, wherein the hydrophilic additive topically coated onto the fiber blend.

16. The nonwoven according to claim 1, wherein the active ingredient is disposed in a film that surrounds an outer surface of the round cross-sectional shaped spunbond fibers and non-round cross-sectional shaped spunbond fibers.

17. A nonwoven comprising:
(a) at least a first spunbond nonwoven layer of 100 wt. % of round cross-sectional shaped fibers having an average diameter less than 10 microns; and
(b) an active ingredient disposed substantially at a surface of the round cross-sectional shaped fibers;
wherein the nonwoven is devoid of a meltblown layer; and
wherein the first nonwoven has a strike through time that is less than 10 seconds for all three insults when tested per WSP 70.7(05); and wherein the first nonwoven layer has a theoretical surface area of greater than about 4200 cm² per gram.

* * * * *

UNITED STATES PATENT AND TRADEMARK OFFICE
CERTIFICATE OF CORRECTION

| | | |
|---|---|---|
| PATENT NO. | : 11,065,160 B2 | Page 1 of 1 |
| APPLICATION NO. | : 15/208845 | |
| DATED | : July 20, 2021 | |
| INVENTOR(S) | : Sven Krister Erlandsson et al. | |

It is certified that error appears in the above-identified patent and that said Letters Patent is hereby corrected as shown below:

On the Title Page

Column 2, under U.S. Patent Documents, "5,361,784 A 11/1994 Kinder" should read --6,361,784 B1 03/2002 Brennan et al.--.

In the Claims

In Claim 4, Column 19, Line 4, "fluid, an ingredient that can control the growth an organism," should read --fluid, an ingredient that can control the growth of an organism,--.

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*